United States Patent [19]

Bok et al.

[11] Patent Number: 5,155,041
[45] Date of Patent: Oct. 13, 1992

US005155041A

[54] CULTURE OF *BACILLUS SUBTILIS*

[75] Inventors: Song H. Bok; Sung U. Kim; Kwang H. Son; Seong K. Kim; Young K. Kim; Hang W. Lee; Jee W. Lee, all of Daejeon; Hye K. Kwon, Kyungbuk; Tae S. Jeong, Daejeon, all of Rep. of Korea

[73] Assignee: Korea Research Institute of Chemical Technology, Rep. of Korea

[21] Appl. No.: 698,522

[22] Filed: May 10, 1991

[30] Foreign Application Priority Data

Oct. 31, 1990 [KR] Rep. of Korea .................. 90-17551
Oct. 31, 1990 [KR] Rep. of Korea .................. 90-17552

[51] Int. Cl.$^5$ ............................................. C12N 1/20
[52] U.S. Cl. .................................................. 435/252.1
[58] Field of Search ...................................... 435/252.1

[56] References Cited

U.S. PATENT DOCUMENTS 4,931,398  6/1990  Kimura ........................... 435/252.1

OTHER PUBLICATIONS

Vater, Lipopeptides, an attractive class of microbial survactants, 1986, 12–18.

*Primary Examiner*—Douglas W. Robinson
*Assistant Examiner*—Deborah K. Ware
*Attorney, Agent, or Firm*—Timothy R. Kroboth

[57] ABSTRACT

The present invention provides a novel microorganism, *Bacillus subtilis* subspecies Krictiensis, and its mutant, *Bacillus subtilis* subspecies Krictiensis M 18-91; and a novel antifungal complex, KRF-001, produced from said microorganisms. The present invention also provides a process for producing said complex by culturing or fermenting said microorganisms and a process for purifying said complex to a desired degree of high purity.

2 Claims, No Drawings

CULTURE OF *BACILLUS SUBTILIS*

BACKGROUND OF THE INVENTION

1. Field of the Invention

The present invention relates to novel microorganisms belonging to the *Bacillus subtilis* subspecies and a novel antifungal complex produced therefrom, which has a variety of useful applications such as a low toxicity agricultural fungicide, a therapeutic agent against fungal infections, a food preservative, a skin moisturizing agent and the like. The present invention also relates to processes for producing said complex from said microorganisms.

2. Description of the Prior Art

Antifungal agents are generally divided into two groups: those which are derived from microbial organisms and those which are chemically synthesized. In the former category, for instance, in 1939, Oxford et al. isolated griseofulvin from the culture of *Penicillium griseofulvum*[see Oxford, A. E., Raistrick, H. and Simonart, P., Biochem. J., 33:240(1939)], which was initially developed as a pesticide and then further developed to be used as an effective oral preparation for the treatment of dermatophytosis; in 1950, nystatin was separated from Actinomycetes by Hazen, et al. [see Hazen, E. L. and Brown, R., Science, 112:423(1950)]; and, in 1955, amphotericin B was isolated from Actinomycetes by Gold, et al.[see Gold, W., Stout, H. A., Pagano, J. F. and Donovick, R., Antibiot. Ann., 1956:579(1955)]. As for the latter category, such comunds as 5-flurocytosines and ketoconazoles were recently developed.

While the chemotherapy for bacterial infections made a great deal of progress, similar results were not achieved in the case of treating fungal infections. Accordingly, development efforts for antifungal agents active against a broad spectrum of fungi including Candida and Aspergillus with little side-effects continued.

As a result, in the early 1960's, various agricultural fungicides were developed; and relatively high toxic pesticidal compounds were replaced with new antifungal agents such as: blasticidin S and kasugamycin for controlling leaf blast of rice[see Takeuchi, S., Hirayama, K., Ueda, K., Sakai, H. and Yonehara, H., J. Antibiotics, 11A:1-5(1958); and Umezawa, H., Okami, Y., Hishimoto, T. Suhara, Y., Hamada, M. and Takeuchi, T., J. Antibiotics, 18:101-108(1965)]; polyoxin and validamycin, both effective against sheath blight[see Isono, K., Nagatsu, J., Kawahima, Y. and Suzuki, S., Agric. Biol. Chem. 29:848-854(1965); and Iwasa, T., Yamamoto, H. and Shibata, M., J. Antibiotics, 23:595-602(1970)]; and mildiomycin useful in controlling barley's powdery mildew[see Harada, S. and Kishi, T., J. Antibiotics, 31:519-524(1978)].

Despite these limited successes, however, needs have continued to exist for the discovery of non-toxic antifungal agents having a broad spectrum of activity.

SUMMARY OF THE INVENTION

In accordance with the present invention, it has been discovered that a novel antifungal complex which has the desired characteristics of both broad antifungal activity and low toxicity can be produced by employing a novel microorganism isolated from the nature and its mutants.

A primary objective of the present invention is, therefore, to provide a antifungal cyclic peptide complex having low toxicity, which is referred to as "KFR-001" hereinafter.

Another objective of the present invention is to provide a novel microorganism, *Bacillus subtilis* subspecies Krictiensis(ATCC 55079), and one of its mutants, *Bacillus subtilis* subspecies Krictiensis M 18-91(ATCC 55078), which are capable of producing the above complex.

A further objective of the present invention is to provide novel processes for producing said complex in a high yield and for purifying said complex to a desired high degree of purity.

DETAILED DESCRIPTION OF THE INVENTION

The present invention relates to a novel KRF-001 complex which comprises cyclic peptide components A, B, C, D, E and F of structural formula (I) (SEQ ID NO.:1):

$$(\beta\text{-AA})\ R(CH_2)_8CHCH_2CO-NH \to Asn \to Tyr \to Asn \to Gln \to Pro \to Asn \to Ser \to \text{(back to }\beta\text{-AA)}$$
(I)

wherein
R is $CH_3CH_2CH_2-$ for component A;

$CH_3CH_2CH-$ for component B;
$\ \ \ \ \ \ \ \ \ \ \ |$
$\ \ \ \ \ \ \ \ \ \ CH_3$ $(CH_3)_2CHCH_2-$ for component C;
$(CH_3)_2CHCH_2CH_2-$ for component D;
$CH_3CH_2CH_2CH_2CH_2-$ for component E;

$CH_3CH_2CHCH_2CH_2-$ for component F;
$\ \ \ \ \ \ \ \ \ \ \ \ \ |$
$\ \ \ \ \ \ \ \ \ \ \ CH_3$ Asn means asparagine;
Gln means glutamine;
Tyr means tyrosine;
Pro means proline;
Ser means serine; and
AA means amino acid.

The arrows employed in describing formula (I) (SEQ ID NO.:1) above represent a peptide bond formed as a result of dehydration, i.e., $$-\overset{O}{\underset{\|}{C}}-NH-,$$

between the carboxyl terminus present in the amino acid located on the tail side of an arrow, e.g., asparagine, and the amino terminus present in the amino acid located on the head side of the arrow, e.g., tyrosine, shown on the first line of formula (I) (SEQ ID NO.:1).

Novel KRF-001 complex of the present invention has been found to contain approximately 40% component A, 16% component B, 20% component C, 14% component D, 7% component E and 2% component F, according to analyses conducted employing high performance liquid chromatography (HPLC); and also, these components A to F have the molecular weights of 1042, 1056, 1056, 1070, 1070 and 1084, respectively, as confirmed by analyses using FAB-MS(Jeol Co., Model DX 303, positive ionization, argon gas, gun voltage 3 KV, emission 30 mA). In addition, amino acid analysis has revealed that each of the six components contains the moieties of Gln, Ser, Pro, Tyr, $\beta$-AA, and Asn in the molar ratio of 1:1:1:1:1:3.

Furthermore, it has been discovered that the specific structure of said lipophilic $\beta$-AA has a direct impact on the antifungal activity of KRF-001. In this connection, GC-MS(gas chromatography-mass spectrometry) analysis performed on the acidolizates of KRF-001 has confirmed that the $\beta$-amino acid has the molecular structure of $C_{14}H_{29}NO_2$ for component A; $C_{15}H_{31}NO_2$ for components B and C; $C_{16}H_{33}NO_2$ for components D and E; and $C_{17}H_{35}NO_2$ for component F. Further, $^1$H-NMR analysis has confirmed the side chain structure in $\beta$-amino acids of KRF-001 to be as follows:

| Component | $^1$H-NMR $\delta$ CH$_3$ | Terminal structure |
|---|---|---|
| A | 0.9(3H, t) | normal-type |
| B | 0.9(6H, m) | anteiso-type |
| C | 0.9(6H, d) | iso-type |
| D | 0.9(6H, d) | iso-type |
| E | 0.9(3H, t) | normal-type |
| F | 0.9(6H, m) | anteiso-type |

In addition, the sterochemical configuration of the amino acids, i.e., either L-form or D-form, constituting KRF-001, may be determined by utilizing, for each moiety of Tyr, Ser, Pro and Gln, a method employing an enzyme such as D-amino acid oxidase, L-amino acid oxidase, L-glutamate oxaloacetate transaminase and L-glutamate decarboxylase; and, for the three moieties of Asn, by using CD(circular dichroism) spectrum analysis (by using JASCO J-20C, 0.1N HCl). Such analyses have thus further enabled to confirm and refine the structural configuration of formula(I) (SEQ ID NO.:1) to be as:

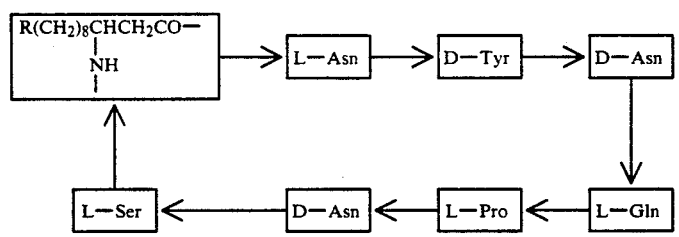

(I')

The arrows employed in describing formula(I') above have the same meaning as defined before.

The KRF-001 complex of the present invention can be produced in an aerobic fermentation process employing the novel microorganism of the present invention, Bacillus subtilis subsp. Krictiensis and its mutants including M 18-91, which are further described below.

A wild type strain of Bacillus subtilis was isolated from various soil samples collected around Mt. Kyeryong, Chungcheongnamdo, Korea. The isolated strain, which was found to be capable of producing said antifungal agent, KRF-001, was named Bacillus subtilis subspecies Krictiensis and deposited on Jul. 26, 1990 with American Type Culture Collection under the deposit number of ATCC 55079.

The present invention further involves mutants of the wild strain, which are also capable of producing the antifungal complex KRF-001. The mutation was carried out by exposing the suspension of the parent strain in caffein solution to UV light, followed by screening the resulting mutants by way of measuring their antifungal activity to ultimately select five strains, i.e., M 18-91, M 26-87, M 27-8, M 28-9 and M 31-139. Among the five strains, M 18-91 is most preferred because of its desirable biological productivity, named as Bacillus subtilis subspecies Krictiensis M 18-91, and deposited on Jul. 26, 1990 with American Type Culture Collection under the deposit number of ATCC 55078. Specific procedures for the mutation are presented below.

The identification of the microorganisms was carried out in accordance with the method described in Bergey's Manual of Systematic Bacteriology, 2, Williams & Wilkins Co.(1986). The novel microorganisms of the present invention were identified as generally similar to the standard strain of Bacillus subtilis (ATCC 6633), except that there are some differences in the spore position, negative oxidase reaction and cell size; and the morphological and physiological characteristics thereof are summarized Tables 1 and 2 hereof.

TABLE 1

Morphological and cultural characteristics of Bacillus subtilis subsp. Krictiensis (ATCC 55079)

| | Characteristics |
|---|---|
| Cell | rod-type, existing as a single cell of 0.8–1.0 $\mu$m $\times$ 2.0–6.0 $\mu$m or as a pair thereof; Gram-positive |
| Spore | ellipsoidal, subterminal with the sporangium not swollen |
| Motility | positive |
| Growth on nutrient agar (pH 6.8) | abundant, forming opaque, creamy colony, producing no pigment |
| Growth on potato-dextrose agar (pH 5.6) | abundant, forming opaque, creamy colony, producing no pigment |
| Growth on nutrient broth (pH 6.8) | normal |
| Growth on potato-dextrose broth (pH 5.6) | abundant |
| Growth temp. on nutrient agar | 15 to 60° C. |
| Growth pH on nutrient broth | pH 5 to 10.5 |

TABLE 2

Comparison of physiological characteristics between the standard strain (ATCC 6633) and the novel microorganism (ATCC 55079) of the present invention

| Physiological Characteristics | Bacillus subtilis (ATCC 6633) | Bacillus subtilis subsp. Krictiensis |
|---|---|---|
| Catalase reaction | + | + |
| Oxidase reaction | + | − |
| Voges-proskauer test | + | + |
| Methyl red | − | − |

TABLE 2-continued

Comparison of physiological characteristics between the standard strain (ATCC 6633) and the novel microorganism (ATCC 55079) of the present invention

| Physiological Characteristics | Bacillus subtilis (ATCC 6633) | Bacillus subtilis subsp. Krictiensis |
|---|---|---|
| Citrate-utilizing Koser medium | + | + |
| Citrate-utilizing Christensen medium | + | + |
| Utilization of propionic acid | − | − |
| Nitrate reduction | + | + |
| Indol formation | − | − |
| Hydrogen sulfide formation | − | − |
| Urease reduction | + | + |
| Starch hydrolysis | + | + |
| Casein hydrolysis | + | + |
| Gelatin hydrolysis | + | + |
| Salt acceptability | 0 to 10% | 0 to 7% |
| Growth in the presence of 0.001% lysozyme | + | − |
| Growth at pH 5.7 | + | + |
| Arginine degradation | − | − |
| Tyrosine degradation | − | − |
| Phenylalanine deamination | − | − |

KRF-001 of the present invention can be obtained by culturing the above microorganisms in an aqueous nutrient medium containing sources of assimilable carbon and nitrogen under an aerobic condition, until a recoverable amount of said complex is obtained. The nutrient medium may also contain mineral salts and an antifoaming agent.

Preferred sources of carbon which may be employed in the nutrient medium are carbohydrates such as glucose, fructose, starch, mannitol and the like. Other sources which may be employed are maltose, sucrose, etc. In addition, complex nutrient sources such as molasses, corn meal, oat meal and the like may also serve as the carbon source. These carbon sources may be used either individually or in combination in the medium.

Preferred sources of nitrogen are complex sources such as yeast extracts, soybean meal, corn steep liquor, corn gluten meal, peptone and the like. Inorganic nitrogen sources such as ammonium salts (e.g., ammonium sulfate, ammonium phosphate, etc.) can also be used. The various sources of nitrogen can be used either alone or in combination in the medium.

The carbon and nitrogen sources are generally employed in combination. Mineral salts may be added to the medium such as (but not limited to) calcium carbonate, sodium or potassium phosphate, sodium or potassium chloride, magnesium salts, copper salts, and the like. In addition, if necessary, an antifoaming agent such as silicon series may be added, especially if severe foaming in the culture medium occurs.

The preferred process for producing the KRF-001 complex comprises inoculating spores or vegetative cells of the microorganisms into a suitable medium; and then cultivating the same under an aerobic condition.

The procedures described hereinbelow represent a preferred illustrative embodiment of the present invention; however, it should not be taken to limit its scope. The fermentation procedure employed was to first inject, as a seed, one vial (1 ml) of *Bacillus subtilis* subsp. Krictiensis stored at −80° C., into a LBG (luria bertani glucose) medium to be described below. The inoculated medium was then cultured in a rotary shaker at a temperature of not higher than 30° C., an agitation rate of 200 rpm and pH 7.0 for 4 to 6 hours.

Thereafter, the fermentation was conducted at a temperature not higher than 30° C. and pH 7.0, with the agitation rate of 400 rpm and aeration velocity of 1 vvm, by employing a 14 l top-driving type tank fermenter (Marubishi MJ-N type) or an 18 l bottom-driving type tank fermenter (B. Braun Biostat E type), while the fermentation medium was preferably controlled to maintain the pH at a range of 7±0.2 by injecting 5N HCl and/or 5N NaOH into the fermenter.

However, for the mutant M 18-91, the fermentation was conducted without having to adjust the pH.

In this connection, when the fermentation process was carried out with the parent strain or its mutant in a complex medium containing sucrose as the carbon source, whose composition is described in Examples 3 and 4 hereof, at 30° C., pH 7.0, 400 rpm and 1 vvm, the fermentation yield of KRF-001 from the parent strain reached its peak during a period of 35 to 42 hours, while that from its mutant M 18-91 reached its maximum level in about 12 to 18 hours after starting the fermentation even if no adjustment of pH was made. As shown in Table 3 and Example 4, mutant M 18-91 produce KRF-001 in an amount more than two times the amount produced by the parent strain.

TABLE 3

The yield comparison of KRF-001 between the parent and mutant strain M 18-91

| Strain | dry weight (g/l) | purity (%) | product weight (g/l) | dry cell weight (g/l) | yield (p/x)* |
|---|---|---|---|---|---|
| Mutant M 18-91 | 2.56 | 25 | 0.64 | 10.35 | 0.062 |
| Parent strain | 1.0 | 25 | 0.25 | 6.68 | 0.037 |

*p/x means product weight/dry cell weight

As stated above, there are several noticeable differences between the parent strain and the mutant M 18-91. First, M 18-91 exhibits a much higher productivity of KRF-001 without having to control the pH of the medium. Secondly, M 18-91 grows faster than the parent strain; and also has a higher cell density. Accordingly, M 18-91 takes much less time to obtain a same amount of KRF-001 compared with the parent strain. Therefore, M 18-91 is more preferred than the parent strain.

After completion of the fermentation, the fermentation broth was centrifuged by employing a refrigerating centrifuge (Sorvall RC5C, GS-3 rotor) at about 5° C. and 7000 rpm for 20 minutes; the cells were discarded; and the pH of the supernatant was adjusted to 6.5 or 7.0.

Thereafter, complex KRF-001 in crude form was isolated from the supernatant by employing isoelectric precipitation or adsorption chromatography as follows:
1. Isoelectric precipitation: A given amount of 5N HCl or 5N $H_2SO_4$ (5-20 ml/l -broth) was added to the cell-free supernatant at once; and the resultant was then thoroughly mixed by way of agitation. When the pH of the mixture reached about 3.0 to 3.5, it was allowed to precipitate at around 5° C. After 2 to 18 hours, the supernatant was discarded; and the precipitate was centrifuged (Sorvall RC5C, GS-3 rotor) at 5° C., 7000 rpm for 10 minutes (purity 20 to 30%).

2. Adsorption chromatography: The supernatant containing the KRF-001 was fed into a column packed with Amberlite XAD-7 resin (Rohm & Haas); and the adsorbed KRF-001 was eluted with 98% methanol to give a fraction containing the KRF-001.

The crude KRF-001 thus isolated from the fermentation broth was then passed through a partition chromatography column charged with silica gel to obtain an active fraction of the crude complex.

Subsequently, the active fraction thus obtained was subjected to a preparative thin layer chromatography ("TLC") using an appropriate developing solvent such as a buthanol/ethyl acetate/water mixture (6:1:1, v/v), chloroform/methanol/aqueous ammonia (15%)/isopropanol mixture (4:3:2:1, v/v), methanol/acetonitrile mixture (1:1, v/v), 100% ethanol, etc., most preferably, said buthanol/ethyl acetate/water mixture, to recover a substance having the intrinsic $R_f$ value of the antifungal complex KRF-001, i.e., 0.36 for the buthanol/ethyl acetate/water mixture, 0.57 for chloroform/methanol/aqueous ammonia (15%)/isopropanol mixture, 0.75 for 100% ethanol and 0.53 for methanol/acetonitrile mixture (1:1, v/v).

The substance thus recovered was then fractionated by employing an appropriate gel filtration chromatography column which has a high resolution power in the fractional range of molecular weight 1000-2000; and is compatible with an organic solvent, such as Sephadex LH-20, Sephadex LH-60, etc., most preferably, Sephadex LH-20. The elution was carried out using a polar organic solvent such as methanol, ethanol, etc., most preferably, methanol.

As the final purification step, the fractionated substance was injected into a high performance liquid chromatography apparatus (Perkin-Elmer, Co) employing an appropriate reverse phase column, e.g., Rsil $C_{18}$ column, $\mu$-Bondapak, etc., most preferably, Rsil $C_{18}$ column, to obtain the pure KRF-001.

In this connection, the presence or formation of KRF-001 in a crude sample prepared or fermentation broth could be detected by employing the TLC. Silica gel 60 F 254 with thickness of 0.2 mm (Merck Co.) was employed as a TLC plate; and the mixture of chloroform, methanol, aqueous ammonia (15%) and isopropanol (4:3:2:1, v/v) was used as a developing solvent. In this solvent system, the $R_f$ value of KRF-001 measured was 0.57; whereas the $R_f$ value was 0.75 when ethanol alone was used as the developing solvent; and 0.53, when a 1:1 mixture by volume of methanol and acetonitrile was used.

The presence of KRF-001 could also be confirmed by detecting a fluorescent spot by exposing the TLC plate under a UV lamp and/or a yellow spot upon iodine treatment.

The quantity of KRF-001 and its antifungal activity was further measured by employing a bioautographic method using *Pyricularia oryzae* as the test microorganism as follows.

First, the activity of pure KRF-001 samples was correlated or expressed in terms of the diameter of their inhibitory zones; and this correlation data was used as the standard for measuring the quantity or carrying out the quantitative analysis of KRF-001 present in, e.g., a fermentation broth.

Having established the standard correlation data, the quantitative analysis of a crude KRF-001 complex was carried out as follows. A sterilized, stainless steel cylinder was placed on a potato dextrose agar plate inoculated with the test microorganism. The filtrate of a fermentation broth containing the KRF-001 complex (filtered through a 0.22 $\mu$m Milipore filter) was pipetted into a bottomless cylinder. After culturing for 1 or 2 days, the diameter of the inhibitory zone was measured with the cylinder removed.

The antifungal activity of KRF-001 of the present invention was investigated by the standard protocol described below.

Determination of Minimum Inhibitory Concentrations:

A slant culture agar such as PDA (potato dextrose agar), Sabouraud's agar, YM (yeast malt) agar and V-8 juice agar was inoculated with various fungi; and cultured at 24° to 30° C. for one day to two weeks. 5 ml of distilled water was added; and the resulting spore suspension was used as the inoculum.

A two fold serial dilution of the spore suspension to be tested was mixed with a fermentation medium for various fungi to make the concentration to 100 to 0.195 $\mu$g/ml; and the mixture was distributed on a petridish having the diameter of 5 cm to solidify the same. The solidified medium was inoculated with one loopful of said inoculum; and cultured at 24° to 30° C. for 1 to 4 days. The minimum inhibitory concentration (MIC) was defined as the concentration that inhibits the growth of a fungus as observed with a naked eye. The results are shown in Table 4 below.

As can be seen from Table 4, KRF-001 of the present invention possesses a broad spectrum of antifungal activities against fungi, particularly *Pyricularia oryzae, Candida albicans* or *Trichophyton mentagrophytes*, comparable to that of commercially available antifungal agents, while exhibiting a much lower toxicity as further demonstrated below.

TABLE 4

| Test Organism | Antifungal Activity of KRF-001 (MIC: $\mu$g/ml) | | | | | | |
|---|---|---|---|---|---|---|---|
| | KRF-001 | amphotericin B | nystatin | cycloheximide | griseofulvin | kasugamycin | polyoxin B |
| *Botrytis cinerea* | 6 | 3 | 1.5 | 50 | 25 | >100 | >100 |
| *Cercospora kikuchi* | 12 | 100 | 12 | 100 | >100 | >100 | >100 |
| *Fusarium oxysporum* | 25 | 50 | 12 | 50 | >100 | >100 | >100 |
| *Fusarium roseum* | 12 | 6 | 6 | 25 | >100 | >100 | >100 |
| *Glomerella glycine* | 25 | 25 | 6 | 25 | >100 | >100 | >100 |
| *Phytophthora capsici* | >100 | 25 | 100 | 0.8 | 100 | >100 | >100 |
| *Phytophthora parasitica* | >100 | 50 | 100 | 1.5 | 25 | >100 | >100 |
| *Pyricularia oryzae* | 3.0 | 0.2 | 0.8 | 3.0 | >100 | 25 | >100 |
| *Rhizoctonia solani* | 6 | 3 | 1.5 | 12 | 100 | >100 | >100 |
| *Rhizopus* sp. | 50 | 100 | 100 | >100 | >100 | >100 | >100 |
| *Asperillus fumigatus* ATCC 164264 | 50 | 1.5 | 12 | 50 | >100 | >100 | >100 |

TABLE 4-continued

Antifungal Activity of KRF-001 (MIC: μg/ml)

| Test Organism | KRF-001 | amphotericin B | nystatin | cycloheximide | griseofulvin | kasugamycin | polyoxin B |
|---|---|---|---|---|---|---|---|
| *Cladosporium carrionii* ATCC 1624 | 50 | 50 | 50 | >100 | >100 | >100 | >100 |
| *Coccidioides immitis* ATCC 34020 | 3 | 0.4 | 6 | >100 | >100 | >100 | >100 |
| *Epidermopyton floccosum* ATCC 38486 | 3 | 0.4 | 1.5 | >100 | 1.5 | >100 | >100 |
| *Microsporum canis* ATCC 11622 | 3 | 1.5 | 1.5 | >100 | 6 | >100 | >100 |
| *Microsporum gypseum* | 6 | 0.8 | 3 | >100 | 3 | >100 | >100 |
| *Sporothrix schenkii* ATCC 10212 | 25 | 50 | 25 | >100 | >100 | >100 | >100 |
| *Trichophyton mentagrophytes* ATCC 9533 | 3 | 0.8 | 3 | >100 | 3 | >100 | >100 |
| *Trichophyton ruburum* | 6 | 0.8 | 3 | >100 | 1.5 | >100 | >100 |
| *Candida albicans* ATCC 102310 | 12 | 1.5 | 6 | >100 | >100 | >100 | >100 |
| *Cryptococcus neoformans* ATCC 36556 | 6 | 0.4 | 3 | 3 | >100 | >100 | >100 |
| *Saccharomyces cerevisiae* NRRL Y-139 | 6 | 0.8 | 3 | 0.2 | >100 | >100 | >100 |

Preliminary Toxicity and Irritation Test:

Preliminary skin irritation test was performed as follows. Two male rabbits of 4 month old (weight 2 to 3 kg) were selected and bruised or cut in a size of 2.5 cm×2.5 cm at four parts. The bruised and non-bruised parts were treated with the solution of 5 g of KRF-001 in 5 ml of distilled water for 24 hours. After one week, no specific irritative reaction was observed either at the bruised or the non-bruised parts.

As for the acute oral toxicity test of KFR-001, seven male ICR mice of 7 to 8 week old (weight 35±5 g) and seven female ICR mice of 7 to 8 week old (weight 25±5 g) were used. KRF-001 was administered orally with sonde at the concentrations of 500, 1000 and 5000 mg/weight kg to each group consisting of 2 to 3 mice.

Within two weeks, only one mouse in one male group (three mouse group) receiving 5000 mg/weight kg died at the third day after administration. While the dead mouse exhibited common clinical symptoms before death, the survivors exhibited no distinct symptoms. Also, no noticeable loss of weight was observed in any of the groups.

As demonstrated above, KRF-001 exhibited comparatively low toxicity even when applied directly. $LD_{50}$ of KRF-001 was estimated as over 5000 mg/kg based on the above acute toxicity test. This indeed represents a much lower toxicity in comparison with such other widely used fungicides as amphotericin B[$LD_{50}$ in mice (mg/kg): 88 i.p.; 4 i.v.] and nystatin[$LD_{50}$ in mice (mg/kg):~200 i.p.][see The Merck Index, 10th ed., 85, 967-968 (1983)]

Effect of KRF-001 for Preserving Fruits:

The effectiveness of KRF-001 for its ability to preserve fruits was tested using strawberries. Mellow strawberries were harvested and washed with distilled water to remove the soil. Two groups of strawberries were infected with the spores of gray mold: a first group without any treatment of KRF-001; and a second group after immersion in a culture solution of KRF-001 at the concentration of 100-200 ppm for 10 minutes. After both groups were kept in an incubator at 25° C. for one week, the first group of strawberries without KRF-001 treatment was spoiled, while the second group with the treatment remained fresh.

It is also apparent that KRF-001 can be used as a moisturizing agent in cosmetic, chemical and food technologies, in view of the fact that KRF-001 is highly soluble in water, methanol and ethanol, etc.; stable at elevated temperatures; and hydroscopic to the extent of gelation of powdery KRF-001 on exposure to a room condition.

Furthermore, it can be used as an antifungal and antiseptic agent in animal feedstuff or chemical preparations such as cleanser and disinfectant.

The following examples are provided to further illustrate some of the specific embodiments of the present invention, without limiting its scope.

EXAMPLE 1

Construction of mutant *Bacillus subtilis* subsp. Krictiensis M 18-91(ATCC 55078)

This example is intended to show how mutant M 18-91 may be prepared in accordance with the present invention.

LBG medium(trypton 1%, yeast extract 0.5%, NaCl 1%, glucose 1%) was inoculated with the parent strain; and then the culture solution was harvested at the end of logarithmic growth phase. The precipitated cells were diluted with distilled water until the absorbance of 1.0 at 550 nm was monitored. Then, an equal volume of 10 μM caffein solution was added; and the resulting suspension was exposed to UV light for 1 minute.

The irradiated suspension was spread on a PDA plate; and the colonies formed were used as test strains (6045 strains). After culturing these strains in 100 ml LBG medium at 30° C. for 40 hours, those strains exhibiting a larger growth inhibition ring than the parent strain on a high density ($2 \times 10^5$ spores/ml) *P. oryzae* plate were selected. The selected 212 strains were cultured for 40 hours in a fermentation medium; and sixteen strains were selected by the same selection process described above. Once again, the selected sixteen strains were cultured in 100 ml of fermentation medium in a 500 ml Erlenmeyer flask; and five strains, i.e., M 18-91, M 26-87, M 27-8, M 28-9 and M 31-139, were selected by the same bioassay.

Among the above five strains, M 18-91 was selected because of its superior productivity of KRF-001; named as *Bacillus subtilis* subspecies Krictiensis M 18-91; and deposited on Jul. 26, 1990 with American Type Culture Collection under the deposit number of ATCC 55078.

EXAMPLE 2

Preparation of Inoculum

The following LBG medium was prepared for use in the slant cultures of Bacillus subtilis subsp. Krictiensis ATCC 55079 and its mutant ATCC 55078:

| Ingredient | Amount (g in 1 l of distilled water) |
|---|---|
| Glucose | 10 |
| Bacto-trypton | 10 |
| Bactoyeast extract | 5 |
| NaCl | 10 |

The pH of the medium as prepared was adjusted to 7.0 before autoclaving.

The cells of each microorganism were suspended in a fresh LBG medium made up of the above identified ingredients; and, an equal volume of glycerol was added thereto (final cell density, $A_{550}=0.01$). 1.0 ml or 0.5 ml of the resulting mixture was injected into 100 to 200 sterilized vials (Nunc Co.) in aliquots and stored in a freezer at $-80°$ C. for subsequent use.

One vial (1 ml) of Bacillus subtilis subsp. Krictiensis was taken from the freezer at $-80°$ C., thawed and inoculated into 100 ml of the above LBG medium in a 1 l bottom-baffled flask (Bellco, Co.), which had been sterilized and cooled to the room temperature. The inoculated medium was cultured in a rotary shaker at 30° C., pH 7.0, and 200 rpm for 4 to 6 hours to obtain the seed culture for subsequent fermentation.

EXAMPLE 3

Production of KRF-001 from Bacillus subtilis subsp. Krictiensis (ATCC 55079)

A 14 l top driving type tank fermenter (Marubishi MJ-N type) was used; and two production media, i.e., one complex medium and one synthetic medium with the following compositions, were employed.

| Ingredient | Complex medium | Synthetic medium |
|---|---|---|
| Sucrose | 30.0 g | 20.0 g |
| Soyton | 10.0 g | — |
| Yeast extract | 5.0 g | 4.0 g |
| $(NH_4)_2SO_4$ | — | 4.0 g |
| $K_2HPO_4$ | 0.5 g | 0.5 g |
| $MgSO_4$ | 0.5 g | 0.5 g |
| trace elements | | |
| $MnCl_2$ | 4 mg | 4 mg |
| $CaCl_2$ | 5 mg | 5 mg |
| $FeSO_4.7H_2O$ | 25 mg | 25 mg |
| Distilled water | 1 l | 1 l |
| pH after autoclaving | 7.0 | 7.0 |

When the growth of the seed culture obtained in Example 2 reached the point where the absorbance at 550 nm was within the range of 0.1 and 0.5, the whole culture solution was aseptically transferred to a 14 l tank fermenter containing 8 l of the complex medium. The pH, temperature, aeration velocity and agitation rate of the fermentation tank were set at 7.0, 30° C., 1 vvm and 400 rpm, respectively. After two days, cooling water($10°-15°$ C.) was circulated to cool the fermentation broth, which was then centrifuged. Thereafter, the cells were discarded; and the supernatant was fed into a XAD-7 column, while adjusting the pH to 7.0 with 5N HCl or 5N NaOH. The elution of adsorbed KRF-001 with 100% methanol gave 12 g of yellowish-brown crude KRF-001(purity, 25%).

EXAMPLE 4

Production of KRF-001 from Bacillus substilis subsp. Krictiensis M 18-91(ATCC 55078)

For mass production of KRF-001, a 100 l top-driving type tank fermenter was used. The compositions of the production media used are shown below.

| Ingredient | Complex medium (g/l) | Industrial medium (g/l) |
|---|---|---|
| Sucrose | 30 | 30 |
| Soyton | 10 | — |
| Pharmamedia | — | 20 |
| Yeast Extract | 5.0 | — |
| $K_2HPO_4$ | 0.5 | 0.5 |
| $MgSO_4$ | 0.5 | 0.5 |
| $MnCl_2$ | 4 mg | 4 mg |
| $CaCl_2$ | 5 mg | 5 mg |
| $FeSO_4.7H_2O$ | 25 mg | 25 mg |

2000 ml of the M 18-91 seed culture solution obtained in Example 2 was aseptically transferred to a 100 l tank fermenter containing 70 l of a medium as prepared. The fermentation was carried out at 30° C., aeration velocity of 1 to 2 vvm and agitation rate of 200 to 250 rpm without any pH control. In case of excess foaming, an anti-foaming agent, e.g., ten-fold diluted silicon series(silicon 30%, Korea Ginseng Co., Ltd.), was added.

The results thus obtained showed a higher fermentation speed than that of the parent strain employed in Example 3: said M 18-91 mutant in the complex medium yielded about 60 g of KRF-001 (purity 25%) after 17 hours' fermentation. When soyton was replaced by Pharmamedia(i.e., when the industrial medium was used), the productivity was much more increased to afford 150 g of crude KRF-001 after 16 hours' fermentation(purity 25%).

EXAMPLE 5

Purification of KRF-001

The fermentation broth obtained, e.g., in Example 4, was purified as follows. About 4 l of the fermentation broth was fed into a 4 l Amberlite XAD-7 column($9 \times 90$ cm, Rohm & Haas Co.); and the impurities were removed by flowing two times the bed volume of distilled water through the column at the rate of 40 ml/min. Subsequently, the column was eluted with two times the bed volume of methanol (8 l). The eluted fractions to be tested for their activity were combined, concentrated under a reduced pressure, e.g., 10 mmHg, and lyophilized to provide the yellowish-brown active material.

After the above procedure was repeated four times, about 15 g of crude yellowish-brown KRF-001 was obtained from 16 l of the fermentation broth.

Subsequent purification was carried out by employing a chromatography column on silica gel. 300 g of silica gel(Article No. 7734, Merck Co., U.S.A) was charged into a column($4 \times 50$ cm) using chloroform. The curde KRF-001 obtained was dissolved in a minimal amount of methanol-chloroform(3:7) mixture and was adsorbed into the silica gel. The elution of KRF-001 was carried out by flowing 750 ml of the methanol-chloroform mixture(3:7) and 2100 ml of methanol-chloroform(1:1). The lyophilization gave 7 g of crude KRF-001.

KRF-001 thus obtained was further purified on a preparative TLC plate using buthanol/ethyl acetate/water(6:1:1) as the developing solvent. 5 g of the substance having the $R_f$ value of 0.36 was recovered as the active material, which was further purified twice on a Sephadex LH-20 column (0.8×90 cm). The substance was dissolved in a small amount of methanol and applied to the column. The elution was carried out at the rate of 0.2 ml/min. using methanol as the eluant. The lyophilization of the fraction containing the active substance gave 1 g of white active material.

As the final purification step, each component of KRF-001 was separated by high performance liquid chromatography(Perkin-Elmer Co.) using Rsil $C_{18}$ column(10 μm, 10×250 mm, Alteck Co.). Said 1 g sample was dissolved in 35% acetonitrile and injected into the column at the concentration of 10 mg/ml. The elution of the sample was carried out with 35% acetonitrile for first 30 minutes; and then gradually increasing the eluant concentration up to 50% acetonitrile for 50 minutes thereafter. The flow rate was controlled at 4 ml/min; and absorbance at 225 nm of UV light was monitored. Peaks having the $R_f$ values(min) of 22.8, 33.8, 38.7, 45.5, 46.5 and 49.8 were found to have biological activity, representing components A, B, C, D, E and F, respectively. 210 mg of component A, 30 mg of component B, 90 mg of component C, 30 mg of component D, 30 mg of component E and 10 mg of component F were finally obtained. This confirmed that KRF-001 is a complex composed of said six components.

EXAMPLE 6

Structural Determination of KRF-001

Various instrumental analyses were carried out in order to determine the structure of KRF-001, including the following.

Elemental Analysis: Said KRF-001 sample finally purified by HPLC as described above was analyzed for the composition of carbon, hydrogen and nitrogen using an element analyzer(Model 240 C, Perkin-Elmer Co.). KRF-001 was found to contain 52.62% carbon, 6.85% hydrogen and 14.59% nitrogen, respectively.

Amino Acid Analysis: 100 mg of said pure KRF-001 sample was dissolved in 6N HCl and held at 110° C. for 6 hours; and then analyzed for its amino acid content employing an amino acid autoanalyzer(Waters Co.). KRF-001 was found to contain Asn, Gln, Ser, Pro, Tyr and β-AA, in the molar ratio of 3:1:1:1:1:1.

Infrared Spectra: 2 mg of said pure KRF-001 sample was mixed with 200 mg of KBr; and the mixture was spread onto a disc. The disc was analyzed by using a ratio record infrared spectrophotometer(Model No. 1420, Perkin-Elmer Co.). Said KRF-001 sample exhibited bands at 3300 to 3500 $cm^{-1}$, 2700 to 3000 $cm^{-1}$ and around 1660 $cm^{-1}$, which indicated the presence of NH group, CH group and carbonyl group, respectively.

Mass Spectra: The molecular weights of KRF-001 components were determined using a JEOL DX-303 mass spectrophotometer in accordance with the FAB(-positive ionization) method. The peaks of ionic molecule $[M+Na]^+$ appeared at 1065, 1079, 1093 and 1107, which indicated the molecular weights of 1042, 1056, 1070 and 1084, respectively. It was thus verified that KRF-001 is a complex of several analogues having different molecular weights.

Nuclear Magnetic Resonance Spectra: For NMR analysis (Bruker AM-300 and Bruker AM-500), said pure KRF-001 sample was dissolved in $CD_3OD$ and charged into a 5 mm tube. TMS(tetramethylsilane) was used as the internal standard reference substance. $^1H$ NMR spectrometry was carried out by employing NMR spectrometers that operate at 300.13 MHz and 500.13 MHz, respectively; $^{13}C$ NMR spectrometers at 75.473 MHz and 125.75 MHz; and $^{15}N$ NMR spectrometer at 50.67 MHz. The interpretation of $^1H$ NMR spectrum, 2D $^1H$-$^1H$ Cosey spectrum, 2D $^1H$-$^{13}C$ correlation spectrum, 2D $^1H$-$^{15}N$ reverse-correlation spectrum confirmed the presence of amino acids such as tyrosine, asparagine, serine and proline.

Physical Properties of KRF-001: The complex is highly soluble in water and methanol, while scarcely soluble in hexane, which indicates its hydrophilic nature. Furthermore, KRF-001 is comparatively stable at pH ranges of 1.0 to 11.0; and also stable for a period of time at elevated temperatures, e.g., for about five hours at 100° C., and about fifteen minutes at 121° C.

It will be apparent to those skilled in the art that certain changes and modifications can be made to this invention without departing from the spirit or scope of the invention as it is set forth herein.

What is claimed is:

1. A biologically pure culture of *Bacillus subtilis* subsp. Krictiensis(ATCC 55079).

2. A biologically pure culture of *Bacillus subtilis* subsp. Krictiensis M 18-91(ATCC 55078).

* * * * *